US008518323B2

(12) United States Patent
Resch et al.

(10) Patent No.: US 8,518,323 B2
(45) Date of Patent: Aug. 27, 2013

(54) APPARATUS AND PROCESS FOR OXIDIZING A VAPOR-PHASE SUBSTRATE WITH LOW DOSE ZONE

(75) Inventors: Darrel R. Resch, Orlando, FL (US); Laura Scott, Orlando, FL (US); Griscom Bettle, III, Sarasota, FL (US)

(73) Assignee: Vapex Environmental Technologies, Inc., Oviedo, FL (US)

( * ) Notice: Subject to any disclaimer, the term of this patent is extended or adjusted under 35 U.S.C. 154(b) by 1265 days.

(21) Appl. No.: 11/597,733

(22) PCT Filed: May 25, 2005

(86) PCT No.: PCT/US2005/018394

§ 371 (c)(1), (2), (4) Date: Feb. 5, 2008

(87) PCT Pub. No.: WO2005/115553

PCT Pub. Date: Dec. 8, 2005

(65) Prior Publication Data

US 2009/0010800 A1 Jan. 8, 2009

Related U.S. Application Data

(60) Provisional application No. 60/574,444, filed on May 25, 2004.

(51) Int. Cl.
*A61L 9/00* (2006.01)

(52) U.S. Cl.
USPC .............................................. 422/5; 422/122

(58) Field of Classification Search
USPC .................. 422/5, 122, 124; 239/424.5, 398, 239/427.5, 428.5, 419.5
See application file for complete search history.

(56) References Cited

U.S. PATENT DOCUMENTS

| | | | | |
|---|---|---|---|---|
| 5,032,619 A * | 7/1991 | Frutin et al. | .................... | 521/55 |
| 5,154,893 A * | 10/1992 | Nakade | ......................... | 422/124 |
| 6,076,748 A * | 6/2000 | Resch et al. | ............... | 239/424.5 |

* cited by examiner

*Primary Examiner* — Davis Hwu

(74) *Attorney, Agent, or Firm* — Scully, Scott, Murpy & Presser, P.C.

(57) ABSTRACT

The present invention relates to an apparatus for the treatment of contaminated air or surfaces in order to remove or oxidize odoriferous gases and deleterious compounds therefrom through the utilization of ozone droplets, and more particularly pertains to the treatment of manufacturing facilities, wet wells, seage installations, buildings, equipment and industrial installations and diverse locales subjected to foul air, in order to remove noxious and potentially toxic vapors and impurities from the air or surfaces through the dissolution of ozone in water to form droplets, and spraying the resultant mixture into the air as a fine aqueous mist. Moreover, the invention is also directed to the provision of a process for eliminating odoriferous or noxious vapor gases and harmful constituents entrained therein from a volume of contaminated air or surfaces through the utilization of ozone dissolved in water by the employment of the inventive treatment apparatus.

39 Claims, 7 Drawing Sheets

APPARATUS AND PROCESS FOR OXIDIZING A VAPOR-PHASE SUBSTRATE WITH LOW DOSE ZONE

CROSS REFERENCE TO RELATED APPLICATION

This application claims the benefit of U.S. Provisional Application No. 60/574,444, filed on May 25, 2004.

BACKGROUND OF THE INVENTION

1. Field of the Invention

The present invention relates to an apparatus for the treatment of contaminated air or surfaces in order to remove or oxidize odoriferous gases and deleterious compounds therefrom through the utilization of ozone droplets, and more particularly pertains to the treatment of manufacturing facilities, wet wells, sewage installations, buildings, equipment and industrial installations and diverse locales subjected to foul air, in order to remove noxious and potentially toxic vapors and impurities from the air or surfaces through the dissolution of ozone in water to form droplets, and spraying the resultant mixture into the air as a fine aqueous mist. Moreover, the invention is also directed to the provision of a process for eliminating odoriferous or noxious vapors or gases and harmful constituents entrained therein from a volume of contaminated air or surfaces through the utilization of ozone dissolved in water by the employment of the inventive treatment apparatus.

The employment of ozone in connection with the use thereof in apparatus and processes for eliminating malodorous and oxidizable constituents from their presence in the air or on surfaces is imbued with various advantages, of which a primary advantage resides in the simplicity of the processes which are required and in the apparatus for implementing the processes. The only basic requirement is the provision of a substantially closed chamber or space which contains the air which is to be treated by means of an ozone generator, and also the elimination of any necessity for the installation of generally expensive filters which require periodic cleaning and replacement, and wherein a further advantage resides in that the products from the vapor which has been purified by the ozonation are generally constituted of carbon dioxide, water soluble sulfate and water which consist of harmless substances. These enclosed spaces or chambers may be lift stations of wet wells, manufacturing locales, scrubber ducts, contaminated buildings and equipment contained therein, among numerous other applications.

Although it is widely known to employ high concentration of ozone for the elimination of odors from air, the latter of which has been fouled by noxious constituents and/or malodorous gases or vapors, for example, such as hydrogen sulfide gas, or other sulfur-containing vaporous substrates, such as mercaptans, dimethylsulfate, and the like, the ozone must be generally evenly dispersed throughout the volume or space of the air being treated and specific concentrations of ozone maintained until the malodorous and noxious constituents entrained in the air have been oxidized, and in effect, odor-neutralized. Such high concentrations of ozone segregate by density such that ozone, being of greater density than air, settles to the bottom of the contained space, corroding the bottom equipment and absenting the upper reaches of the confined space, thereby not eliminating the light malodorous compounds in the top of the head space.

In order to overcome any disadvantages which are encountered in the odoriferous or noxious gas-removal treatment of air, by means of ozone in a preferably continuous mode, advantages may be taken by the ability of ozone being soluble in water, whereby the reaction of ozone with water forms various free radical moieties such as hydroxyl free radicals, superoxides and the like and peroxy radicals which, in turn, further reacts to form hydroperoxide free radical. These compositions comprising hydroperoxide and hydroxyl are strong oxidizers which will readily react with numerous impurities, including microorganisms such as bacteria and viruses, and destroying these by oxidizing the latter and or interrupting their reproductive mechanisms, and wherein ozone is quite normally injected into municipal water supplies as a purifier and disinfectant. Furthermore, it is also important to use ozone in the treatment of lift stations in wet wells, such as those in wet sewage treatment plants, and also in industrial and commercial installations in which waste or polluted water emits odoriferous gases, not to mention constituents which are entrained in the gases such as bacteria and viruses, as well as pollutants encountered in scrubber ducts, contaminated buildings and other manufacturing and industrial installations, and surfaces thereof, and whereby the odors which are generated are extremely objectionable to persons in the immediate vicinity or environs of the particular installations or facilities being treated. In order to be able to eliminate or neutralize the noxious or odoriferous gases which are emitted from the various installations or wet wells, a process of spraying water containing dissolved ozone into the air in the form of sprays of very fine droplets is advantageous in eliminating these gases and impurities in the air in comparison with simply introducing a flow of ozone into the air. The reactions between the ozonated water sprays and gases or impurities contained in the air is extremely rapid, and serves to remove any concerns as to the ozone constituting a health hazard in the environment inasmuch as the ozone contained in the air is generally less than 0.5 parts per million, which is considered to be a permissible level when absorbed by humans.

Furthermore, the dispersing of a spray containing extremely fine droplets of water in which ozone into the air in order to remove odoriferous gases and contaminants is accomplished by causing gaseous ozone to come into contact with the water, and the absorption thereof depends upon the size of the contact surface between the gaseous ozone and water, which also increases the speed at which ozone is absorbed by water in proportion to the size of the contact area.

2. Discussion of the Prior Art

The utilization of spray-forming nozzles which atomize ozone in water has been already well developed in the technology, and industry, whereby patents by the present inventors are of particular significance and advantage. Thus, Erb et al., U.S. Pat. No. 5,337,962 discloses an atomizer device which reduces flowable liquid into an ultrafine dispersion of liquid particles in a propellant gas, and whereby an atomizing spray of ozone may be formed to treat odoriferous or noxious gases in order to remove any odorous properties and/or impurities therefrom.

A more recent development in providing an odor controlling atomizer nozzle device which employs ozone dispersed in water to form minutely sized droplets clearly provides the advantages of rapidly and extensively eliminating odoriferous gases, such as hydrogen sulfide, from the air which has been contaminated with these gases emanating in enclosed spaces from sources such as, for instance, wet wells or diverse locales, is disclosed in Resch et al., U.S. Pat. No. 6,076,748. The disclosures of both of these patent publications are herewith incorporated in their entirety by reference into the present application.

Although the atomizing nozzle disclosed in Resch et al., U.S. Pat. No. 6,076,748 clearly provides an advantageous structure when implementing a process of purifying air, the degree of being capable of removing odoriferous gases and potentially any pollutants in the air stream which are generated in enclosed spaces is generally at an efficacy of up to approximately 90%. Typically, municipal sewers which may include lift stations comprising wet wells may contain of up to 1,000 ppm of $H_2S$ (hydrogen sulfide) gases, although a more typical well may only contain about 50 ppm. These ozonated water spray treatments, although normally adequate in purifying the air in eliminating the odoriferous gases may not fully meet the requirements of more sophisticated customers or residents domiciled in the vicinity of such wet wells, since the high dosage levels of hydrogen sulfide gases generated in some of the wet wells may only be eliminated by up to a 90% reduction, and multiple atomizing nozzles of that type also fail to provide a reduction of the problems emanating from only a 90% improvement to targeted improvements of 99% to 100% in ideal situations. Consequently, a problem which is required to be solved in purification of air and removing odoriferous or noxious oxidizable gases therefrom, for example, such as those constituted of hydrogen sulfide gas or other sulfur-containing gases, or toxic nitrogen containing gases, such as $NH_3$, is to facilitate a degree of purification of the air of up to 99% or 100%; and also to enable residual ozones to be exhausted to acceptable levels, and also to enable the use of industry acceptable measuring apparatus which will sense a true reduction in hydrogen sulfide or other sulfur-containing gases and contaminates contained in the air.

SUMMARY OF THE INVENTION

Accordingly, in order to improve upon the state-of-the-art, the present invention provides a process of oxidizing vapor-phase substrates such as air or various propellant gases with ozonated sprays through the use of an apparatus which, in conjunction with an atomizing nozzle as depicted in U.S. Pat. No. 6,076,748 or of the type which functions similarly to the three fluid nozzle depicted in U.S. Pat. No. 6,076,748, the latter of which is depicted herein by way of example only, creates a spray of small ozonated water particles adapted to react with contaminated air, containing, for example, oxidizable deleterious gases, for instance, gaseous sulfur-containing gases, such as for example hydrogen sulfide ($H_2S$), mercaptans, dimethyl sulfides or nitrogen containing gases, e.g., ammonia, and the like, in order to remove odoriferous gases and therein entrained particulate constituents and/or adjacent impurities, grease, bacteria and viruses from the air or surfaces which are contaminated to an extent which improves upon the level of approximately 90% purification or elimination thereof which is presently attainable in the technology. An extremely important aspect of the invention resides in the ability of the apparatus and process to be able to sanitize gas flows and gas-contacted surfaces passing through the ventilation system of contaminated buildings, as described in more specific detail hereinbelow.

In order to attain the foregoing, the present invention is directed to the provision of various types of apparatus incorporating versions of atomizer nozzle similar in function to that of U.S. Pat. No. 6,076,748 in order to achieve almost ideal purification conditions, wherein particles of ozonated water are employed in sprays of optimized droplet sizes within a range of at or below about 3 microns, thus avoiding the presence of excessively large ozonated droplets which result in the formation of residual unreacted ozone and sulfur-containing gases. To that extent, the present invention also provides for apparatus structure which will remove such large droplets through the incorporation of a slotted vented tube. Moreover, a further aspect of the apparatus resides in a provision of a circulation inducing head which, in conjunction with the nozzle for atomizing ozone and water particles, will further provide for an induced vacuum and increased circulation in a turbulent manner so as to form the small sized wet particles of ozonated water which completely react with contaminants, such for example, sulfur-containing or nitrogen-containing gases in the air, for purifying the latter and eliminating unwanted impurities, gas-generated odors, grease, bacteria and viruses.

Accordingly, it is an object of the present invention to provide an apparatus for the purification of air containing odoriferous gas or of sanitizing contaminated surfaces and particulate impurities entrained therein or deposited thereon, such as grease, bacteria and viruses, through the intermediary of sprays of ozonated water droplets.

Another object resides in the provision of an apparatus which, in combination with an atomizer nozzle of U.S. Pat. No. 6,076,748 or functioning in a manner similar to that of U.S. Pat. No. 6,076,748 or modifications thereof creates conditions which will enable the elimination of oxidizable gases, for instance, such as sulfur-containing or hydrogen sulfide gas, nitrogen-containing gas and the like, and therein entrained impurities from air in enclosed spaces and from surfaces so as to purify the air or sanitize the surfaces to an extent providing an almost total degree of purification thereto.

Another object resides in the provision of a process for oxidizing vapor phase substrates with low dose ozone through the formation of small sized wet particles of ozonated water droplets with the use of the inventive apparatus.

BRIEF DESCRIPTION OF THE DRAWINGS

Reference may now be made to the following detailed description of preferred embodiments of the apparatus for the treatment of contaminated air and surfaces pursuant to the invention, taken in conjunction with the accompanying drawings; in which.

DETAILED DESCRIPTION OF THE INVENTION

Figure 2:
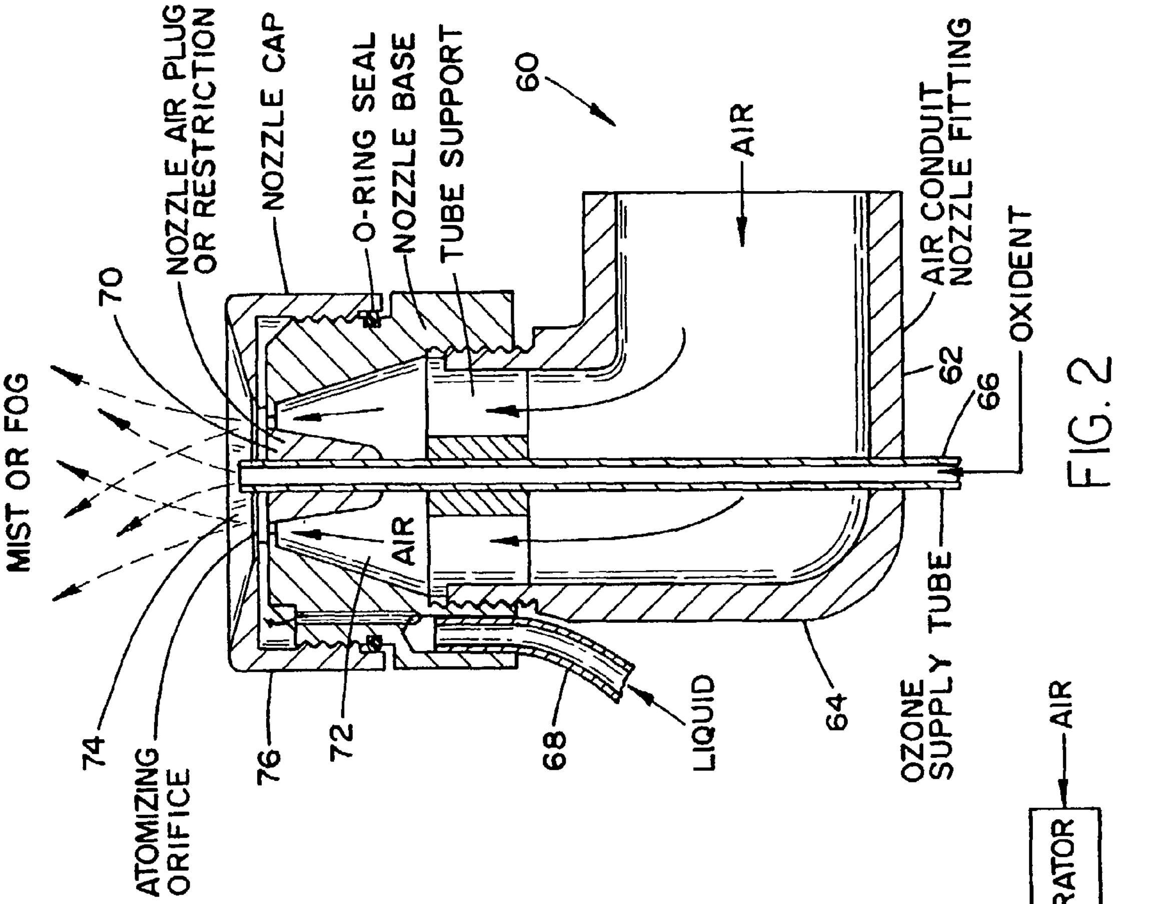
FIG. 2 illustrates a generally diagrammatic sectional representation a modification of the atomizing nozzle shown in FIG. 1 of the drawings with the addition of a propulsion air, cross sectional area reducing means.
Figure 1:
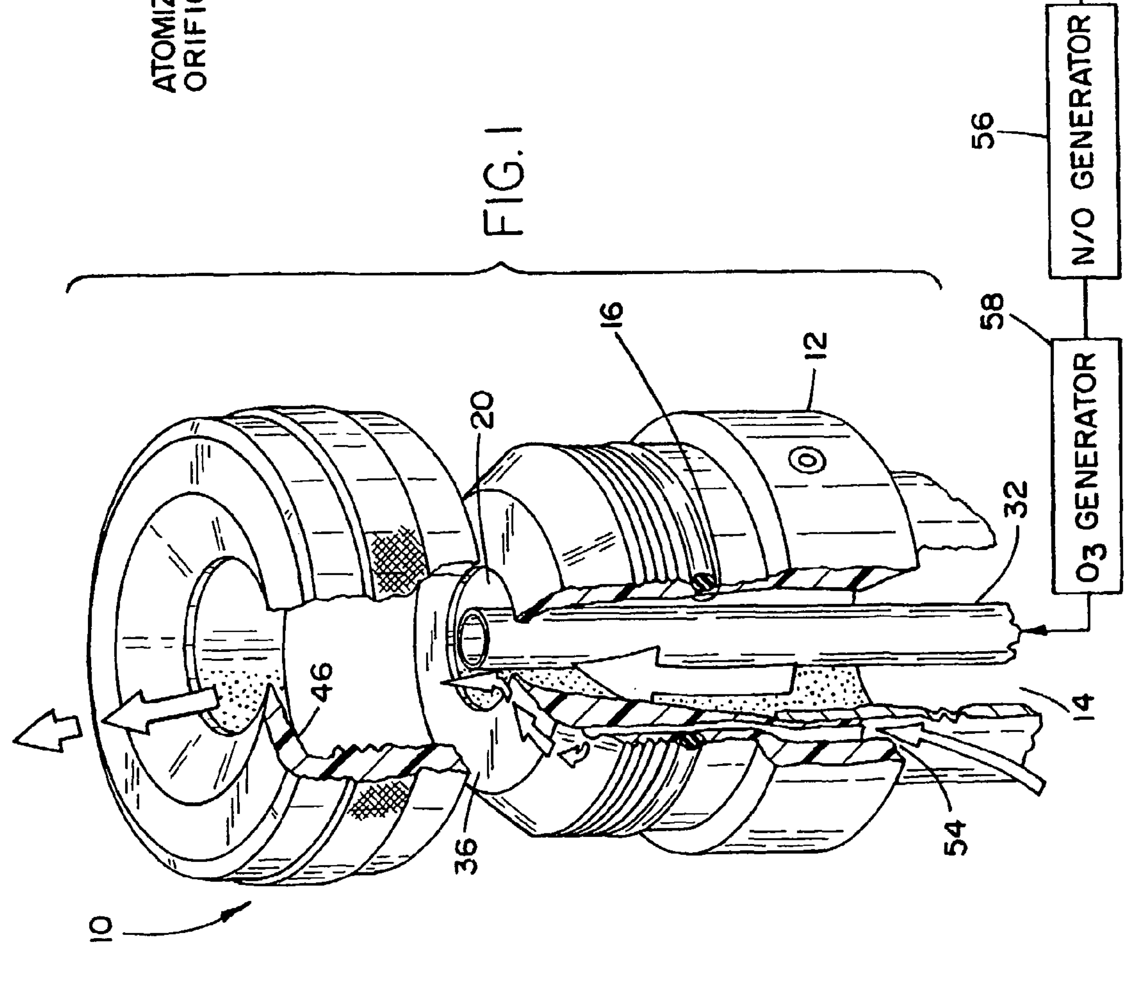
FIG. 1 illustrates a partially sectioned view of an atomizing nozzle for producing a spray of ozonated water droplets, wherein the nozzle is as disclosed in U.S. Pat. No. 6,076,148 or functions in a manner similar to that as disclosed in U.S. Pat. No. 6,076,748, wherein the nozzle is adapted to be utilized in conjunction with the apparatus pursuant to the present invention.

Basically, the air purification apparatus and the process for oxidizing vapor-phase substrate with low dose ozone pursuant to the invention; in effect, by creating small wet particles or droplets of ozonated water which will react with odoriferous gases in order to eliminate the noxious odors therefrom, while also removing therein entrained contaminates and particles including impurities such as grease particles, bacteria and viruses, and also being capable of sanitizing surfaces, utilizes the atomizing nozzle as disclosed in FIG. 1, or the modification thereof as disclosed in FIG. 2 of the drawings.

With reference to FIG. 1, there is shown an atomizer device 10 which is provided for the purification of air or surfaces in diverse locales by utilizing ozone contained in a fine liquid mist, wherein the nozzle device is as described in U.S. Pat. No. 6,067,748, or functions in a manner similar to that as disclosed in commonly owned Resch et al. U.S. Pat. No. 6,076,748, which is described herein by way of example to an extent serving for a background explanation of the present invention. The atomizer device 10, in which the components are represented in an exploded relationship, involves the utilization of a body member 12 having an internal passage or gas conduit 14 through which propellant gas, such as air or other mixtures, as described hereinbelow is constrained to flow. This internal passage 14 is configured to form a converging type nozzle 16 that accommodates the flow of air or some other gas able to properly serve as a propellant gas. The propellant gas 14 can be air obtained from any air supply source, or recirculated air from the treated space. For example, as described below, clean air is supplied to a nitrogen/oxygen generator 56 which forms a desired ratio of these elements. This nitrogen/oxygen mixture is than conveyed into an ozone generator 58 for admixture with ozone and further conveyance into gas conduit 32 as the oxidizing gas.

The gas conduit 14 has an outlet 20 passing through a pair of closely spaced smooth surfaces, first surface 36 and second surface 46, and terminates adjacent the first surface 36. The smooth surfaces 36 and 46 are disposed in a parallel relationship, with a very small spacing existing between the surfaces.

The first smooth surface 36 is disposed in a substantially perpendicular relationship to the gas outlet 20, with an edge of the first surface 36 being disposed closely adjacent the propellant gas flowing through the gas outlet 20. The circularly configured edge of the second smooth surface 46 is set back from the circularly configured edge of the first surface.

An ozone-supplying conduit 32 is centrally disposed within the gas outlet 20, with the conduit 32 serving for the emitting of ozone at a desired location within the gas flowing through the gas outlet.

The foregoing atomizer device 10 is essentially a three fluid nozzle wherein the fluids are constituted of water, air (or other suitable propellant gas) and ozone made from a nitrogen/oxygen mixture so as to form a propellant velocity of preferably about 1,000 feet per second. Water is then added to the fluid stream through a circumferential annulus 54 around the streaming air wherein the latter pulls the water into a balloon until film fragments which are formed of water are of 0 to 3 to 5 to 7 micron size. Centrally located within the nozzle and extending into the zero pressure area thereof is a pipe delivering the ozone which dissolves in the film as it forms into droplets providing a preferable spray angle of about 7° wherein the cone of droplets substantially retains its integrity for a distance of about 11 feet, and thereafter the spray becomes amorphous.

As illustrated in FIG. 2 of the drawings, there is provided a modified atomizing nozzle 60 wherein an air conduit 62, shown in the form of an elbow 64, supplies the nozzle with a flow of air analogous to that of FIG. 1, and an ozone supply tube 66 provides the ozone, while water is added through a conduit 68 in a manner analogous to that of the previous embodiment. However, in this embodiment a plug 70 is provided in the airflow passageway 72 proximate the nozzle outlet or atomizing surface 74 at nozzle cap 76 so as to restrict the amount of airflow. This plug structure which shows the recirculating droplet nozzle and which can be installed in the ceiling of a wet well may also be enclosed in a suitable PVC (polyvinyl chloride) pipe cylinder. The employment of the plug 70 reduces the airflow volume by possibly up to two thirds and in a wet well this will increase the residence time, such increased residence time being important in order to allow for a more complete oxidation of the oxidizable substrate.

Although the air inlet duct or conduit 62 is shown in the form of an elbow 64 which is threadingly attached to the atomizing nozzle 60, it may possess an elongated cylindrical component so as to enable atomizing the nozzle 60 to be positioned deeply in recesses within the space of a wet well above its water level. In this connection, by way of background material, wet wells which are also referred to as lift stations are locations in which sewage is lifted from a lower elevation to a higher elevation, and in the presence of, for example, any sulfate ion present therein, is reduced by sulfate reducing material into hydrogen sulfide gas ($H_2S$), which is an odoriferous and noxious gas. These gases accumulate in the closed head space in wet wells above the water level eventually seeping out and fouling the atmosphere, whereby these gases are to be eliminated or removed from the air by means of the present invention.

Figure 3:
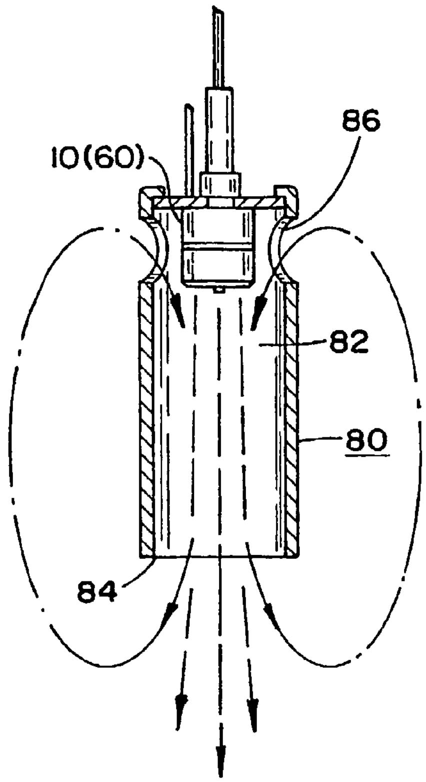
FIG. 3 illustrates a flow circulation inducing head shown in a longitudinal axial sectional view for utilization in conjunction of the atomizing nozzle with either FIG. 1 or 2.

As illustrated in FIG. 3 of the drawings, there is provided a circulation inducing head 80 constituted of a pipe cylinder 82 having an open discharge end 84. One or more apertures 86 are drilled through the side wall of the cylinder, preferably two apertures opposite each other so as to permit recirculating ozonated water droplets to enter the interior of the cylinder. The cylinder 82 is of a sufficient length to allow the discharged cone of spray from nozzle 10 or 60 which is attached thereto at the other cylinder end 86 to facilitate the cone formed by the spray emitted from the atomizing nozzle to intersect the inside diameter of the cylinder and resultingly create a vacuum producing a venturi effect interiorly of the cylinder 82. This vacuum will draw small droplets of 0 to 3 microns in size of ozonated water back into the cylinder 82, and upon these slowly moving droplets being impinged upon by fast moving droplets presently produced by the nozzle, the number of the 0 to 3 micron sized droplet effectively substantially doubles and thereby substantially doubles the surface area of reactive droplets; increasing the mass transfer of agents in the air from the gas phase to a droplet phase and thereby removing further particulate, matter and odors which are absorbed from the malodorous sulfur-containing gas into the ozonated water droplets.

Figure 4:
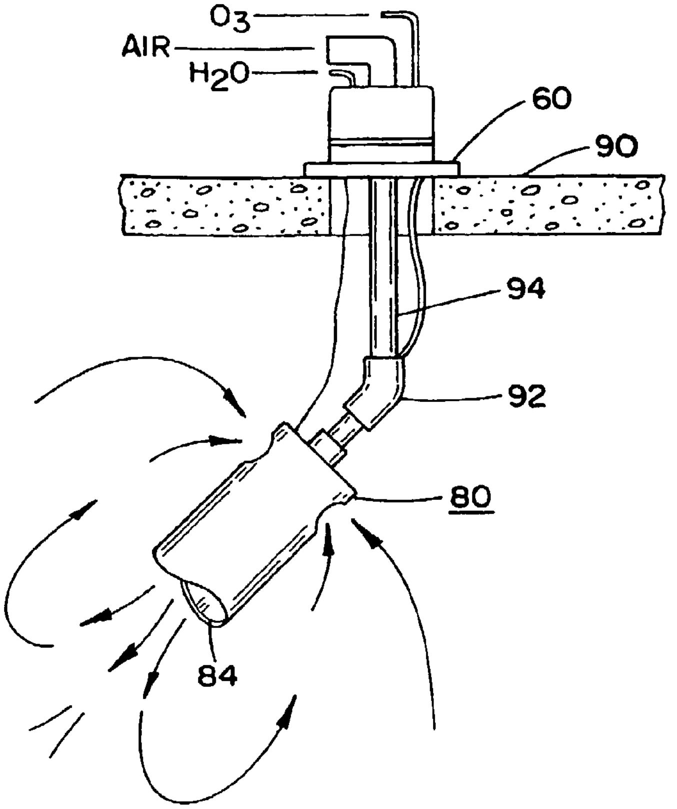
FIG. 4 illustrates generally diagrammatically, a representation of the arrangement of an embodiment of the apparatus as mounted on a cover plate of an enclosed gas-generating enclosed space.

As illustrated in FIG. 4 of the drawings, this shows the arrangement of a nozzle 60 pursuant to FIG. 2 mounted on a slab 90 which covers a wet well or any other enclosed space (not shown), and with the circulation inducing head so extending angled downwardly from a connecting angle piece 92 which is connected to the lower end of a pipe 94. Ozonated water droplets are sprayed from the open lower end 84 of the circulation inducing bead 80 into the air above the water level of the wet well, thereby eliminating or purifying odoriferous gases, such as hydrogen sulfide gas or other noxious gases having contaminants contained therein. As represented in FIG. 4 this shows the nozzle 60 of FIG. 2 mounted on the slab 90 covering the wet well and having the inlet connections for the ozone, air and water provided thereon, although it is also contemplateable that the nozzle may be mounted further downwardly at the upper end of the circulation inducing head 80, as shown in FIG. 3 of the drawings, whereby an atomizing nozzle 10, such as the nozzle as illustrated in FIG. 1 of the drawings or a similar nozzle thereto may be employed in an alternative arrangement.

Figure 5:
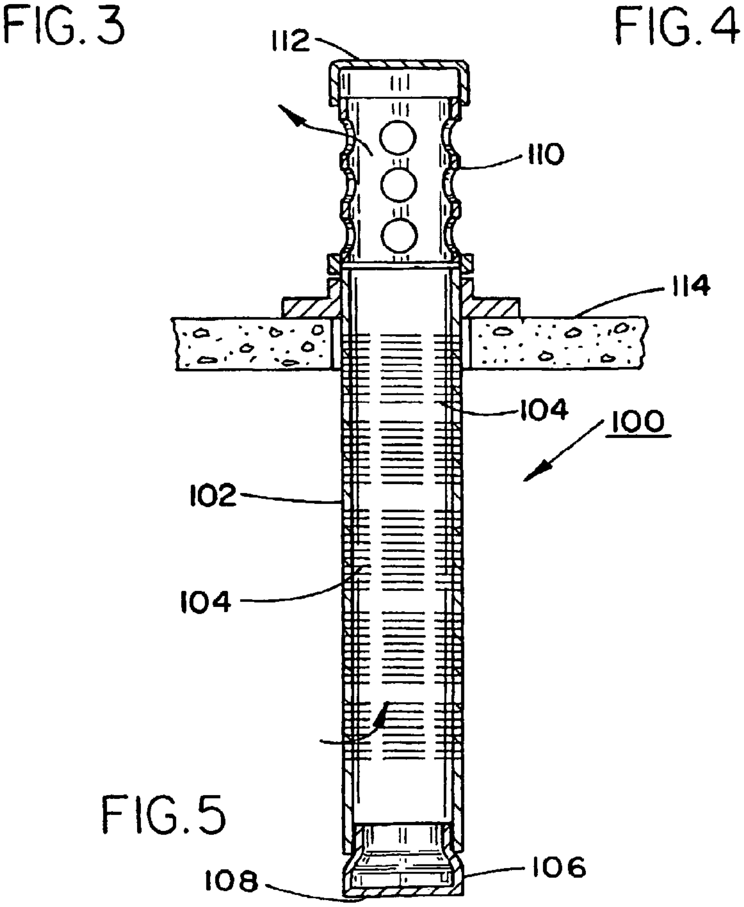
FIG. 5 illustrates generally diagrammatically a condensing vent assembly which is utilized in conjunction with the apparatus of the present invention.

Referring to FIG. 5 of the drawings illustrated is a slotted condensing vent assembly 100 performing a condensing function in connection with the treatment apparatus. The assembly 100 comprises a perforated tube 102 in which the droplet-enriched air flow is adapted pass through a series of thin slots 104 formed along the length thereof into the interior space of the vent tube. Large droplets coalesce in the slots and drip down mostly on the tubular outside surface of the vent and to a lesser extent along the interior surface of the vent tube. Although the large droplets do not propagate a free radical chain reaction in order to admix the ozone with the water and to small size droplets, the large droplets do carry the contaminant gases, such as hydrogen sulfide, and the like, and the ozone into the wet well, where these large droplets are then recycled, thereby reducing the residual load in an exhaust stream. At a lower end, the vent tube 102 has a closure cap 106 with a drain hole 108 therein; whereas at an upper end the vent tube is equipped with an apertured exhaust conduit 110 having a cap 112. The exhaust conduit extends above a cover plate or slab 114 for an enclosed space, for example, a wet well.

The size of the transverse slots 104 extending spaced along the vertical elevation or length of the condensing vent tube assembly may each be approximately 0.02 inches in width, although other widths may also be applicable to permit wet particle-laden air to pass through the slots to provide condensating of the liquefied material, such as water, along the surfaces thereof.

Figure 6:
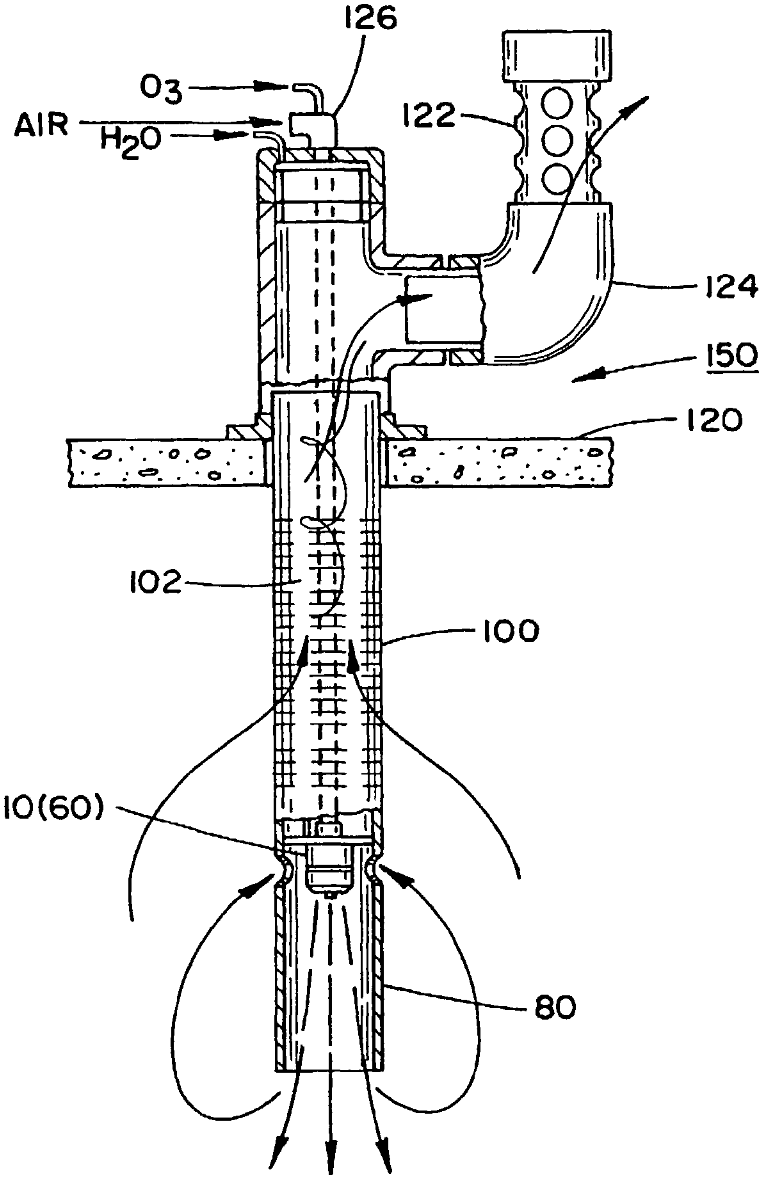
FIG. 6 illustrates, generally diagrammatically, an installation of an apparatus for purifying air or surfaces through ozonated water droplets utilizing a combination of the circulation inducing head and condensing vent assembly as represented in FIGS. 3 and 5 of the drawings.

As illustrated in FIG. 6 of the drawings, this shows the apparatus 150 assembled in an installation with the combination of the slotted vent structure 100 of FIG. 5 and the circulation inducing head 80 attached to the open lower end of the former. Hereby, the slotted vent tube 102 extends upwardly through an opening in a slab 120 covering a wet well or any enclosed space and the like, and wherein there is an upper exhaust pipe section 122 communicating through an elbow connection 124 with the interior of the vent tube. Fastened to the lower end of the slotted vent tube 102 is the circulation inducing head 80 which, as illustrated in FIG. 3 of the drawings, is equipped with an atomizing nozzle 10 or 60. A supply arrangement 126 for supplying the required ozonating droplet-forming constituents, such as a flow of air, water and ozone, is connected to the upper end of the projecting portion of the slotted tube. The functioning of the apparatus produces a turbulent and circulating flow through the slotted tube 102, and through the vacuum forward in the flow circulation inducing head 80 in a manner as described hereinabove produces the flow of the small droplets for absorbing the contaminant gases, e.g., the odoriferous hydrogen sulfide gas or other similar gases. In the lower section of the vent tube 102 there is mounted the nozzle from which an expanding spray cone just intersects the interior wall of the concentric pipe or circulation inducing member 80, thereby creating a vacuum or a venturi effect drawing the small droplets of ozonated water back into this vacuum environment and then causing it to be recirculated so as to further propagate the absorption of the odoriferous hydrogen sulfide gas or other contaminant gas and the removal of entrained contaminants, thereby resultingly purifying and deodorizing the air above the water level of the wet well or of the enclosed space or chamber containing waste water or liquid sewage.

Figure 7:
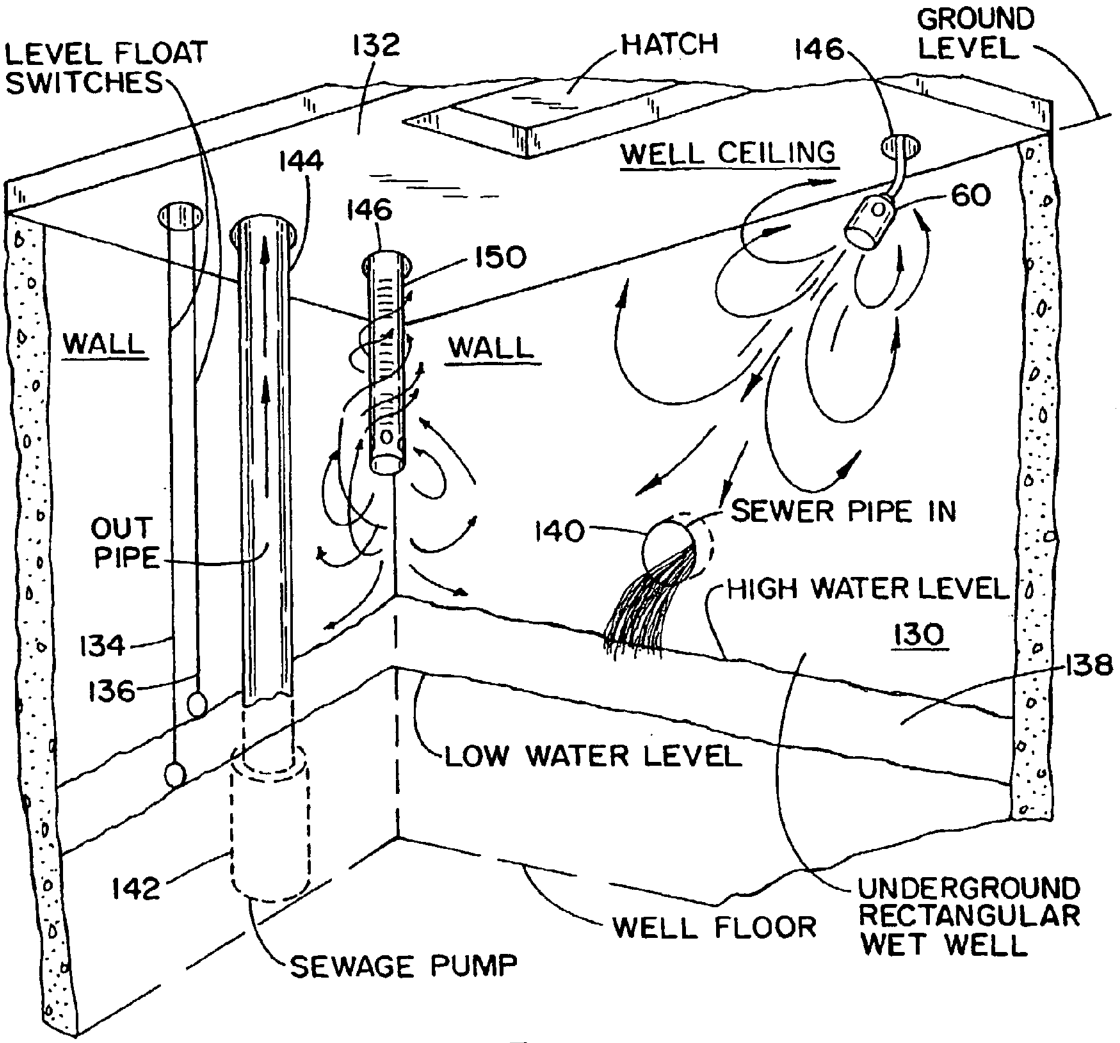
FIG. 7 illustrates, generally diagrammatically, a scenario of an underground wet well equipped with two embodiments of the air purification apparatus pursuant to the invention.

As illustrated in FIG. 7 of the drawings, this shows a typical scenario of a section of an underground wet well 130 wherein a suitable slab 132 having a hatch covers the wet well, as is well known in the sewage treatment technology and in which a liquid level flow switches 134, 136 control the level of sewage water 138 in the well supplied through a sewer pipe 140 by means of a suitable sewage pump 142 which is connected to an outlet pipe 144.

Arranged proximate one corner wall structure of the wet well 130 and extending downwardly through an aperture 146 formed in the slab 132 is an arrangement of a treatment apparatus 150 as illustrated in FIG. 6 of the drawings, whereas at some distance therefrom is a further arrangement of a treatment apparatus with the nozzle arrangement 60 as shown in FIG. 4 of the drawings. In that instance, the nozzle 60 is illustrated as being oriented at an angle of approximately 45° from the vertical; however, it may be directed either vertically down or horizontally and/or in any radial orientation about the circumference thereof. This dual arrangement will provide for a highly efficient purification of the enclosed air space above the water level of the liquid in the wet well. Thus, the ceilings formed by the covering concrete slab and the walls and the water surface in the corners, in which proximity the apparatus and above-mentioned nozzles are positioned, defines a six-sided reaction space possessing two sides which move out and in depending upon the fluctuations in the level of the sewage water. This reaction space defines a continuous stirred tank reactor (CSTR). Thus, by means of the arrangement as shown in FIG. 7 of the drawings, particularly if the vent is exhausted by means of a fan (not shown) a spiral motion of the circulating media is formed interiorly of the slotted vent tube 102 and induces a counterclockwise flow circulation in the CSTR. This motion, in essence, increases the efficiency of the mass transfer in the CSTR thereby providing an increase in efficiency in the removal of the hydrogen sulfide or sulfur-containing gas and in the purification of the air.

An advantage which is derived in this treatment wet wells vehicles is that the use of the nitrogen/oxygen mixture and the ozonated water droplets have an effect on non-gas phase grease which is deposited on the walls of the wet wells or on walls of buildings or on equipment. The process essentially dissolves the solid-state grease. Without wishing to be bound, it is believed that the application of the present process to grease makes it water soluble. Without wishing to be bound, it is believed that the grease is converted into a water-soluble fatty acid which is carried off with sewage liquid or waste water from the wet well. Continued treatment prevents the grease from reforming.

Figure 8:
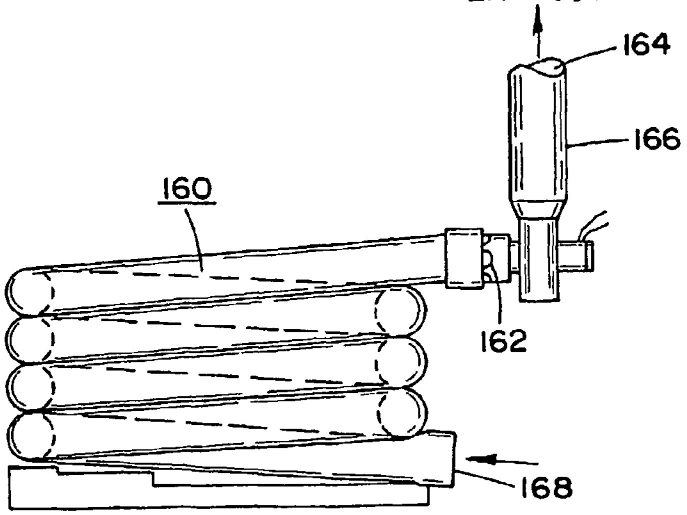
FIG. 8 illustrates, generally diagrammatically, a powered polishing vent unit which is adapted to be employed with an air or surface purification apparatus pursuant to the invention.

Referring to FIG. 8 of the drawings, there is illustrated a tubular coiled ducting 160 having a powered polishing vent which creates a turbulent flow of incoming air and with a vacuum adjustment device 162 being provided proximate an outlet 164 connected to an exhaust conduit 166 which, may in turn, be connected to a suitable exhaust fan (not shown) for drawing the air in at an inlet opening 168, and creating a turbulent flow condition.

Figure 9:
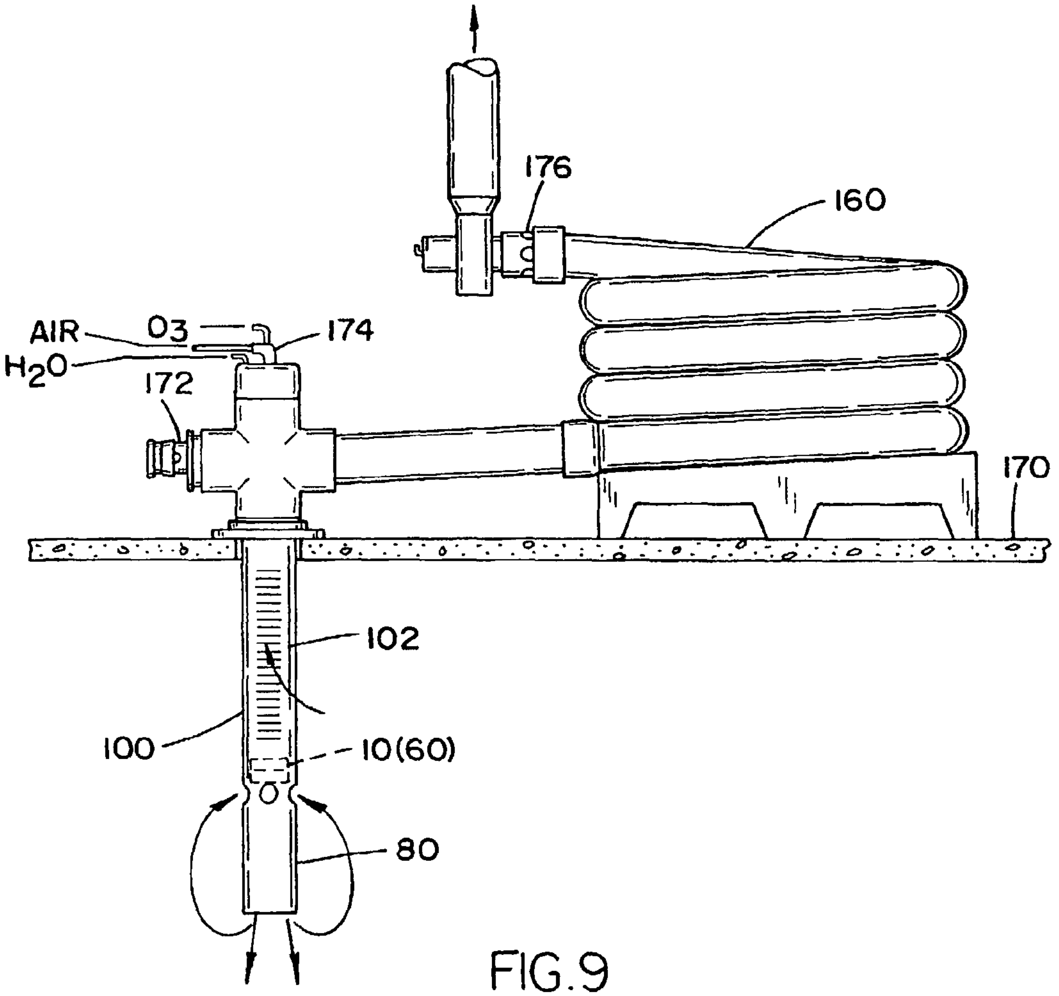
FIG. 9 illustrates, generally diagrammatically, the polishing vent unit of FIG. 8 in conjunction with an air or surface purification apparatus pursuant to the invention.

As illustrated in FIG. 9 of the drawings, the polishing vent 160 provided for by the coiled duct producing the turbulent air flow may be mounted on a slab 170 above a wet well or any suitable enclosed space containing waste water beneath contaminated air or surfaces with hydrogen sulfide gases or other contaminant gases entrained therein. A slotted vent tube 102 and circulation inducing head 80 with nozzle 10 or 60, as in FIG. 6, extend downwardly and at the upper end are connected to a three hole adjustable suction damper or check valve 172 (as applicable) and to an inlet unit 174 for the three way nozzle 10 or 60 by supplying the nozzle which may be positioned in the circulation inducing head 80 with ozone, a flow of water and air. The damper or check valve 172 will assure an adequate airflow through the apparatus. The outlet end of the coiled duct of the polishing vent 160 may be optionally equipped with an adjustable vacuum flow limiter 176 to control the volume of airflow.

As the droplets and the entire flow is drawn upwardly through the coiled tubular scrubber, the turbulence will create an adequate air volume which flows through the plug flow apparatus so as to mix the droplets of ozonated water into the air space above the liquid in the wet well or the enclosed space below the slab.

Figure 10:
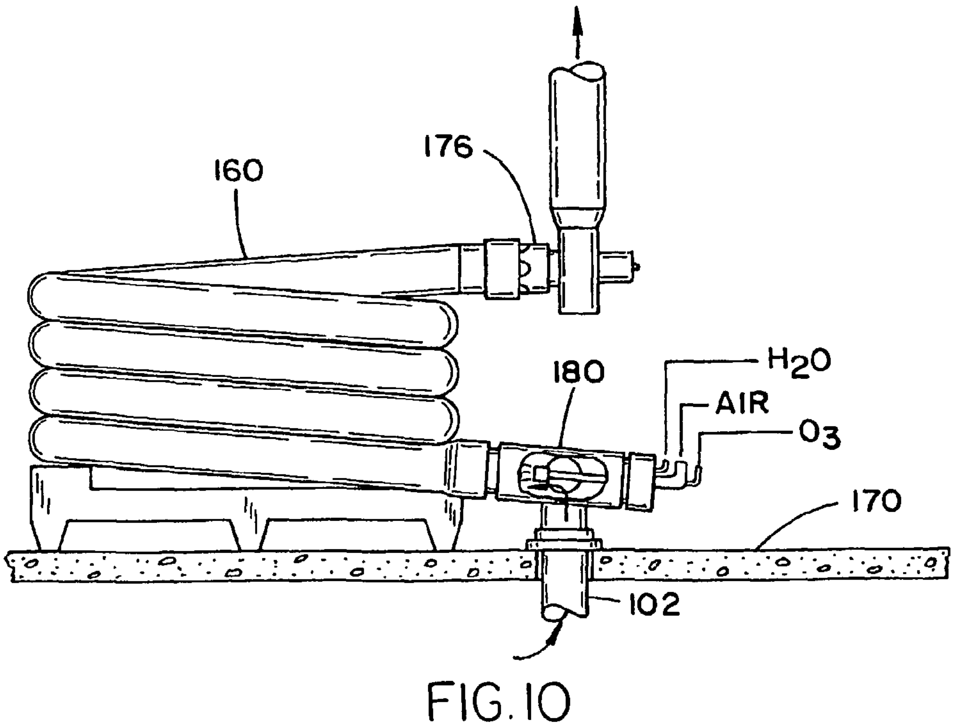
FIG. 10 illustrates a modification of the equipment of FIG. 9 incorporating an ion activation device installed in the polishing vent unit.

In a modification of the apparatus in FIG. 10 of the drawings, which is substantially similar to that shown in FIG. 9, in that instance there is no fog provided in the vented space of the coiled tubular polishing vent 160, and ion activation means 180 is activated so as to remove or control any malodor, microorganism or grease entrained therein. This embodiment of the inventive apparatus has particularly important and advantageous functions in the process of treatment and sanitizing of contaminated buildings and rooms. Hereby, the vent structure 160, as also illustrated in FIGS. 8 and 9 of the drawings, may comprise the duct work throughout a single-story or multi-story or skyscraper building, such duct-work possibly being a component of an air conditioning and/or heating and/or ventilating system. Hereby, small ozonated water droplets can be disposed throughout the contaminated building in the duct work, thereby facilitating the elimination of fungi, bacteria, virus, mold and other microorganisms that are harmful to humans, and which are involved in causing or cause various diseases, such as colds, Legionnaire's Disease and the like, and other malodors and contaminants. Without wishing to be bound, it is believed that the ozone containing water droplets formed in accordance with the present invention or interfere with the reproductive cycle of these harmful microorganisms. This can be readily accomplished with continuously supplying very low doses since the nitrogen/oxygen mixture which is employed allows for very low ozone dosages to be available for lengthy contact times.

The foregoing can be similarly used in decontaminating waste water, scrubber ducts, wherein vent apparatus 160 represents a series of branched ducting. The small droplets are drawn through an inlet branch duct into a main duct and then into a scrubber, thereby decontaminating all of the duct work in a highly efficient manner.

Figure 11:
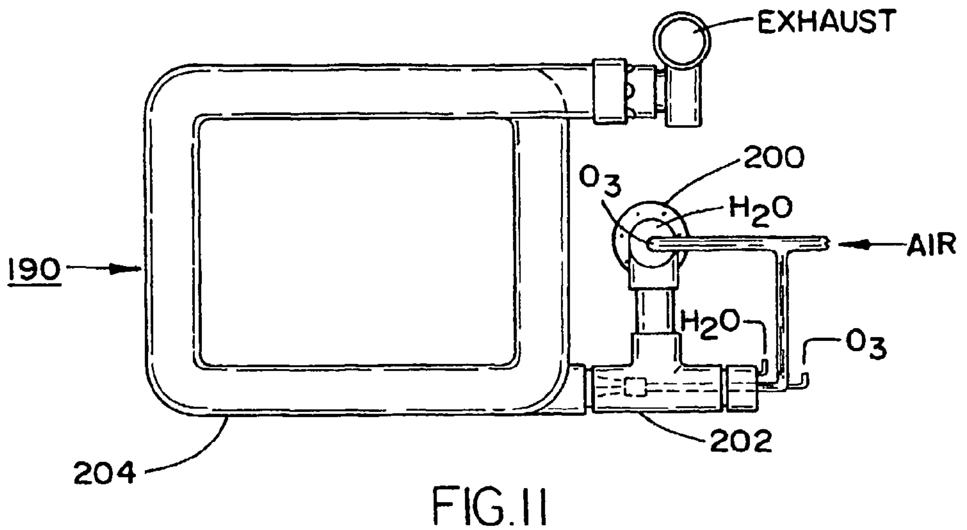
FIG. 11 illustrates a top plan diagrammatic view of a polishing vent with ion activation as shown in FIG. 10 employed in wet well treatment utilizing a two-nozzle system.

In FIG. 11 there is illustrated a top plan view of another combination of an apparatus 190, which looks down on a slotted vent recirculating dual nozzle arrangement as shown in the previous embodiment of FIG. 6 with a second recirculation inducing nozzle aligned with fluid flow and a plug flow reactor. This type of arrangement showing a closed circuit with the combined nozzle units particularly useful for scrubber applications in industrial installations. Hereby, the downwardly oriented nozzle arrangement 200 is directed into the head space above the liquid or odoriferous gas generating media, whereas the horizontally oriented nozzle arrangement 202 is aimed into a scrubber duct 204 which is aligned with the fluid flow.

Figure 12:
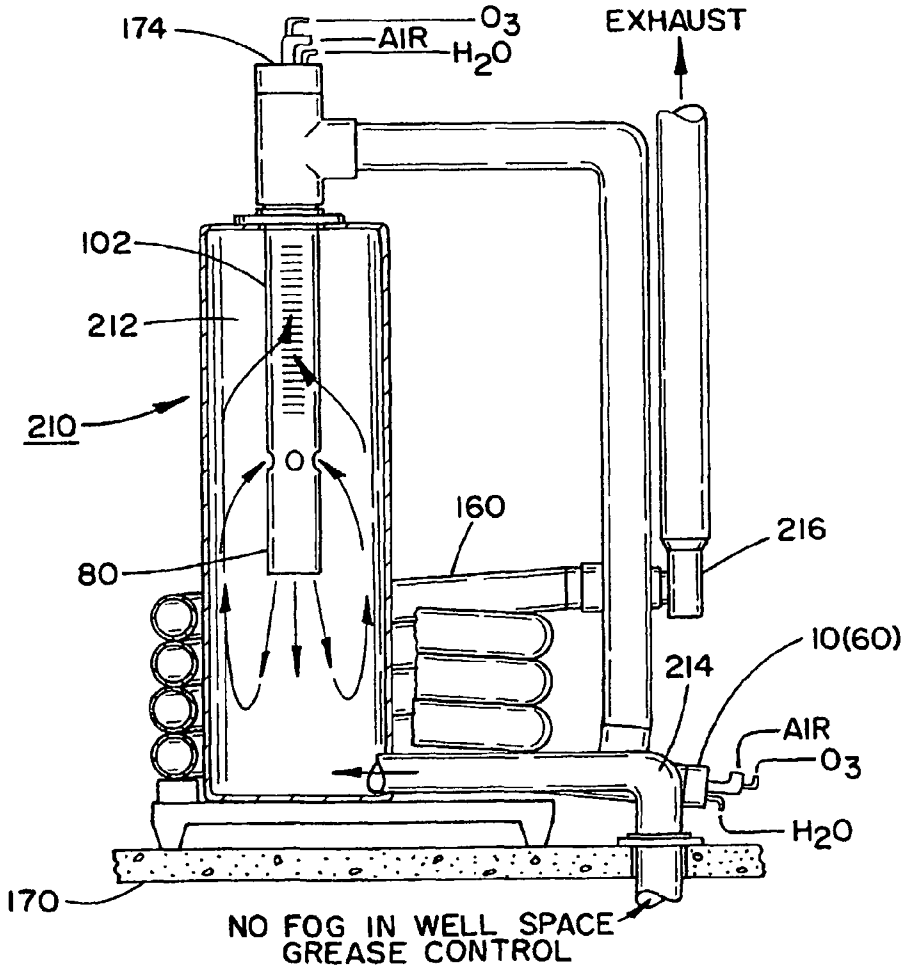
FIG. 12 illustrates, generally diagrammatically, an ion air scrubber utilized in industrial applications and incorporating an air purification apparatus pursuant to the invention.

As illustrated in FIG. 12 of the drawings, in that instance there is shown a vertical ion scrubber 210 wherein the contaminated or fouled air is pulled into a large closed chamber 212 with the slotted vent tube 102 and circulation inducing head 80 having an atomizer nozzle 10 or 60 therein, as shown in FIG. 7 of the drawings, extending downwardly into the closed chamber. This arrangement has the air pulled out from the large closed chamber 212 and into a plug flow apparatus 214 containing a second spray nozzle 10 or 60 spraying into the plug flow reactor. Air is pulled through the entire apparatus through an exhaust fan 216 so as to cause the ozonated water droplets to intermingle with the air and to treat sulfur-containing gases and contaminates which are contained in the air of the enclosed space. This particular type of configuration is utilized with very small wet wells which do not permit sufficient volume to permit an even distribution of the ozone laden water droplets in the head space above the sewage or contaminated water level. For the remainder the functioning and process is identical or similar to that described in the preceding installations of FIG. 9 or 10.

Figure 13:
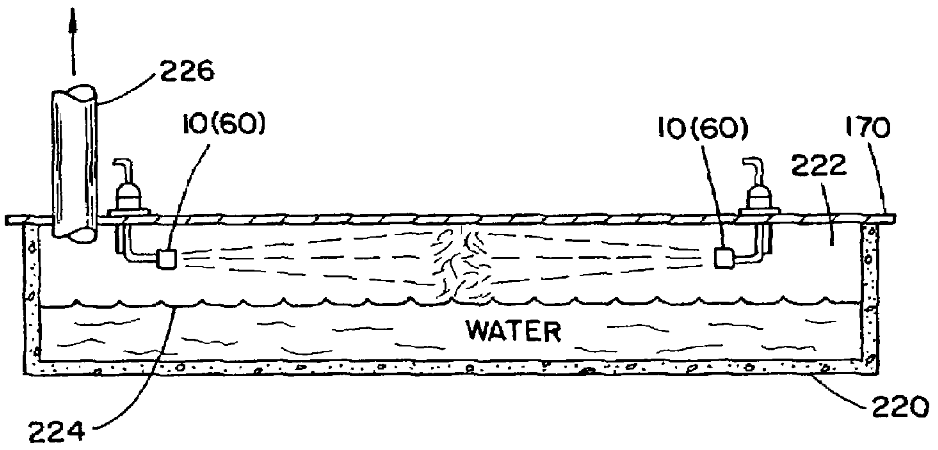
FIG. 13 illustrates in, generally diagrammatically, a shallow well incorporating a multiple nozzle placement scenario wherein a plurality of nozzles directly impinge one another.

As represented in FIG. 13 of the drawings, this illustrates a shallow wet well 220 wherein a turbulent air flow area 222 is formed above a sewage water level 224 and in which a pair of three-fluid atomizing nozzle arrangements 10 or 60 which may be similar of those represented in FIGS. 1 and 2 of the drawings are mounted in the space and oriented in a horizontal manner aimed to spray towards each other such that the droplets from each nozzle impinge on each other before the spray pattern becomes amorphous. As a result of said impinging droplets, the efficiency of impinging sprays is greater than the effect of the same number of nozzles when they do not impinge. Hereby, the conicity of the spray emanating from each of the nozzles and the distance between the mutually facing nozzles, as described hereinbefore is of significance. The direct impingement of the generated droplets from each nozzle against the other results that in the cone integrity distance is such as to effect a droplet oscillation inducing impingement of the droplets from both nozzles. This dual nozzle arrangement covers the area above the sewage water level with the spray of ozonated water particles or droplets to produce a generally complete purification of the air and removal of odoriferous gases and entrained impurities. A vent 226 may be provided, and which may extend to as to be connected to a suitable polishing scrubber (not shown), for example, of the type as is disclosed in either FIGS. 9 and 10 of the drawings.

Figure 14:
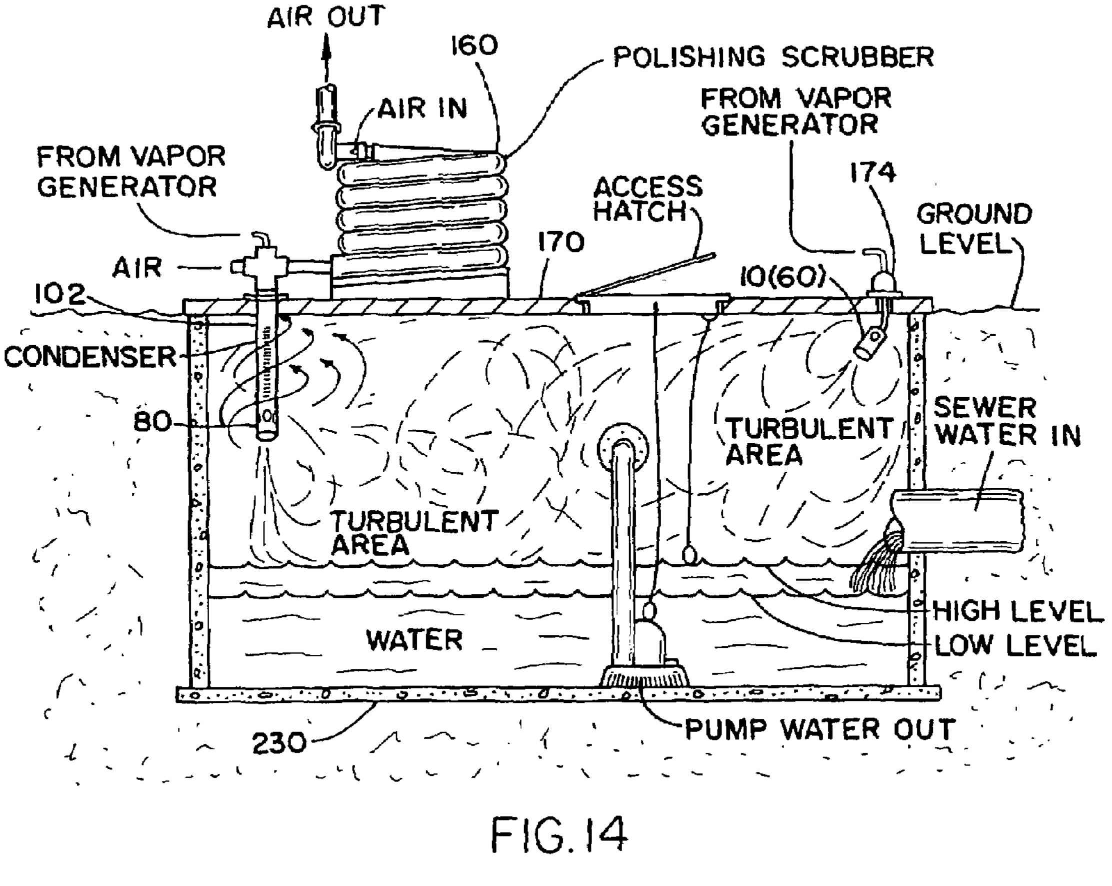
FIG. 14 illustrates a sectioned view representation of a scenario of a portion of a wet well incorporating a plurality of nozzles employed in conjunction with embodiments of the inventive air purification apparatus and a polishing vent unit.

As illustrated in FIG. 14 of the drawings, there is illustrated a further scenario of a wet well 230 showing a two nozzle apparatus arrangement in which a scrubber may be attached to one of the nozzle apparatus, and to a vented tube condenser and a circulation inducing unit as illustrated in FIG. 9 of the drawings, and with a further nozzle structure being provided to extend into the turbulent air region above the water level of the sewage water, wherein the further nozzle apparatus may be such as is described in FIG. 4 of the drawings, and may be oriented in any suitable manner relative to the vertical, horizontal or circumferential directions.

Finally, it is to be noted that the process of implementing the oxidizing of the sulfur-containing gases is highly corrosive in nature so as to necessitate that the components of the apparatus be constituted of corrosion-resistant materials. Such materials, among others, may be fiberglass, polyvinylchloride (PVC), or high-quality stainless steel.

Although the above embodiments illustrate ozone as the feed gas passing through the gas conduit 32 of the nozzle in FIG. 1, other feed gases may be utilized as can other droplet formation means. For example, referring to FIG. 1, in another embodiment, the feed gas is a gas prepared by passing a specific gaseous mixture comprised of oxygen and nitrogen through an ozone generator (58). The specified mixture of nitrogen and oxygen gas is prepared by a nitrogen-oxygen generator (56) of any suitable type as is known in the art. For example, in one embodiment, the mixture is prepared by removing a specified amount of nitrogen from the air using techniques known to one of ordinary skill in the art. It is preferred that the volume ratio of oxygen to nitrogen in the mixture ranges from about 21% oxygen:78% nitrogen, as found in air to about 99% oxygen:1% nitrogen. However, it is more preferred that the mixture comprises at least about 95% oxygen and 5% nitrogen. It is even more preferred that the ratio ranges from about 93% oxygen:7% nitrogen to about 95% oxygen:5% nitrogen, and most preferably the ratio is about 90% oxygen:10% nitrogen. (All of the % of gases are understood to be by volume).

The reaction of the mixture described hereinabove with ozone, especially at a ratio of 90% oxygen:10% nitrogen, provides a longer lasting ozone. The half life of ozone in clear water is about 15 minutes, but when the oxygen content was increased, especially to a mixture of 90% oxygen and 10% nitrogen, measured amounts of ozone were found in the condensate 24 hours after the ozone was generated. Without wishing to be bound, it is believed that the mixture of nitrogen and oxygen form a nitric oxide, which when reacted with ozone forms, a nitrogen oxide moiety with more solubility in water than ozone alone. Without wishing to be bound, it is further believed that the reaction of nitric oxide with ozone forms a $NO_3$. radical which eventually breaks down into ozone over time, thereby prolonging the existence of ozone in the condensate.

What we claim is:

1. An apparatus for the treatment of contaminated air, or surfaces in an enclosed space for the removal of odoriferous oxidizable gases and/or microorganisms and/or non-gas phase grease therefrom utilizing wet particles of ozonated water reacting with the gases, said apparatus comprising:

at least one atomizing nozzle arranged in said enclosed space, said at least one atomizing nozzle being supplied with flows of water, propellant gas, comprised of contaminated or uncontaminated air, and ozone produced from a mixture of nitrogen and oxygen, the water, propellant gas and ozone being admixed to form a spray of ozonated water droplets into said enclosed space;

a circulation inducing head being attached to said atomizing nozzle for increasing the output of said ozonated water droplets reacting with said odoriferous gases so as to eliminate odors emanating therefrom, particulate contaminants entrained in said gases and microbial contaminants; and a slotted vent tube connected to an upper end of said circulation inducing head, said slotted vent tube extending to the exterior of said enclosed space, said slotted vent tube receiving a flow of said contaminated air containing ozonated water droplets through said slots, wherein large-sized droplets coalesce within said slots and drain down along the surfaces of said vent tube and are recycled.

2. An apparatus as claimed in claim 1, wherein said mixture of nitrogen and oxygen feeding the ozone generator means ranges by volume from about 78% nitrogen and 21% oxygen to about 1% nitrogen and 99% oxygen.

3. An apparatus as claimed in claim 1, wherein said circulation inducing head comprises a surrounding solid surface having said at least one atomizing nozzle attached to one end and having an open opposite end;

said surrounding solid surface having at least one aperture formed in the peripheral well so as to facilitate droplets of said ozonated water to recirculate therethrough and create a vacuum in said cylinder, whereby said vacuum draws slower moving of said droplets into said surrounding solid surface which are impinged by rapidly moving droplets from the spray of said at least one nozzle thereby increasing the number of droplets reacting with said gases.

4. An apparatus as claimed in claim 1, said at least one atomizing nozzle includes a plug structure for restricting the flow volume of said propellant gas being admixed with water and ozone to form said ozonated water droplets so as to increase the reaction time of said ozonated water droplets with said gases for eliminating odors and contaminants therefrom.

5. An apparatus as claimed in claim 1, wherein said slotted vent tube propagates a turbulent flow of contaminated air having entrained ozonated water droplets exteriorally of said tube assisting in the mixing of said droplets with said contaminated air before coalescing.

6. An apparatus as claimed in claim 1, wherein said enclosed space comprises a wet well of a sewage treatment facility, said at least one atomizing nozzle being adapted to treat oxidizable gas comprising hydrogen sulfide gas emitted by waste water in said wet well so as to cause said ozonated water droplets to absorb odors and particulate contaminants, bacteria and said virus from said hydrogen sulfide gas for purifying the contaminated air in said space.

7. An apparatus as claimed in claim 6, wherein at least two of said apparati each comprising one said atomizing nozzle in spaced relationship are operative to eliminate odors and contaminants from said emitted hydrogen sulfide gas.

8. An apparatus as claimed in claim 7, wherein a first atomizing nozzle assembly is directed into said enclosed space and a second said atomizing nozzle is directed into a polishing vent installation possessing an ion activation arrangement for wet well treatment.

9. An apparatus as claimed in claim 1, wherein said enclosed space defines a chamber of an industrial site containing oxidizable gas emitting from waste liquids; a polishing vent of a scrubber being operatively connected to said apparatus, said polishing vent including a coiled duct imparting turbulence to an air inlet flow so as to enable the reaction of ozonated water droplets for the elimination of said oxidizable gases in said closed chamber.

10. An apparatus as claimed in claim 1, wherein a polishing vent of a scrubber includes an adjustable vacuum flow limiter and an adjustable suction damper connected to a turbulence-producing coiled vent ducting is operatively connected to said treatment apparatus.

11. An apparatus as claimed in claim 1, wherein said oxidizable gas is present from the group of gases consisting of hydrogen sulfide gas, mercaptans, ammonia, dimethylsulfide, and oxidizable substrates including substituted sulfides.

12. An apparatus as claimed in claim 1, wherein said apparatus is essentially constituted of corrosion-resistant components selected from the group of materials which are consisting of fiberglass, polyvinylchloride, polyethylene, stainless steel and the like materials substantially impervious to attack by sulfur-containing gases.

13. An apparatus as claimed in claim 1, wherein said at least one atomizing nozzle is adapted to be operative in diverse enclosed spaces, such as scrubber ducts, contaminated building, lift stations including wet wells of sewage treatment plants, manufacturing facilities, and the like for eliminating odoriferous gases from contaminated air, and particulate contaminants, grease, bacteria and viruses entrained in the gases.

14. An apparatus as claimed in claim 1, wherein a recirculating atomizing nozzle is directed into a duct installation for duct disinfection wherein measurable ozone exists in the condensate of droplets exiting said ductwork.

15. An apparatus as claimed in claim 1, wherein said mixture of nitrogen and oxygen feeding the ozone generator means ranges by volume from about 93% oxygen and 7% nitrogen to about 95% oxygen and 5% nitrogen.

16. An apparatus as claimed in claim 1, wherein said mixture of nitrogen and oxygen feeding the ozone generator means is about 90% oxygen and 10% nitrogen.

17. A process for the treatment of contaminated air or surface, in an enclosed space for the removal of odoriferous sulfur-containing gases therefrom utilizing wet particles of ozonated water reacting with the gases, said process comprising:

- arranging at least one atomizing nozzle in said enclosed space;
- supplying said at least one atomizing nozzle with flows of water, a propellant gas, comprised of contaminated or uncontaminated air, and ozone produced from a mixture of nitrogen and oxygen;
- forming a spray of ozonated water droplets into said enclosed space by admixing the water, propellant gas and ozone in the at least one atomizing nozzle;
- selectively condensing water droplets larger than 7 microns, present in said spray of ozonated water droplets, whereby said condensed water droplets are removed from said spray of ozonated water droplets; and
- recirculating water droplets equal to or smaller than 7 microns into said spray of ozonated water droplets.

18. A process as claimed in claim 17, wherein said mixture of nitrogen and oxygen ranges by volume from about 78% nitrogen and 21% oxygen to about 1% nitrogen and 99% oxygen.

19. A process as claimed in claim 17, further comprising generating a vacuum for drawing in slower moving of said ozonated water droplets to be impinged by rapidly moving ozonated water droplets from the spray of ozonated water droplets.

20. A process as claimed in claim 17, further comprising restricting the flow volume of said propellant gas being admixed with water and ozone to form said ozonated water droplets so as to increase the time of said ozonated water droplets with said gases to react, eliminating odors, microorganisms and contaminants therefrom.

21. A process as claimed in claim 17, further comprising propagating a turbulent flow of air having entrained ozonated water droplets to assist in the mixing of said droplets with said contaminated air prior to coalescence of said droplets.

22. A process as claimed in claim 17, wherein said enclosed space comprises a wet well of a sewage treatment facility, said at least one atomizing nozzle being adapted to treat hydrogen sulfide gas emitted by waste water in said wet well so as to cause said ozonated water droplets to absorb odors and particulate contaminants, bacteria and said virus from said gas for purifying the air in said space.

23. A process as claimed in claim 22, wherein at least two of said atomizing nozzles arranged in spaced relationship are operative to eliminate odors and contaminants from said emitted hydrogen sulfide gas.

24. A process as claimed in claim 23, wherein a first atomizing nozzle of said at least two atomizing nozzles is directed into said enclosed space and a second atomizing nozzle of said at least two atomizing nozzles is directed into a polishing vent installation possessing an ion activation arrangement for wet well treatment.

25. A process as claimed in claim 17, wherein said enclosed space defines a chamber of an industrial site containing oxidizable gas emitting waste liquids; a polishing vent of a scrubber being operatively connected to said enclosed space, said polishing vent including a coiled duct imparting turbulence to an air inlet flow so as to enable the maintenance of ozonated water droplets for the elimination of said oxidizable gases in said closed chamber.

26. A process as claimed in claim 25, wherein a polishing vent of a scrubber includes an adjustable vacuum flow limiter and an adjustable suction damper connected to a turbulence-producing coiled vent ducting is operatively connected to said atomizing nozzle.

27. A process as claimed in claim 17, wherein said odoriferous sulfur-containing gases is present from the group of gases consisting of hydrogen sulfide gas, mercaptans, ammonia, dimethylsulfide, and oxidizable substrates including substituted sulfides.

28. A process as claimed in claim 17, wherein apparatus for implementing said process is essentially constituted of corrosion-resistant components selected from the group of materials consisting of fiberglass, polyvinylchloride, polyethylene, stainless steel and the like materials which are substantially impervious to attack by sulfur-containing gases.

29. A process as claimed in claim 17, wherein said at least one atomizing nozzle is adapted to be operative in diverse enclosed spaces, selected from the group consisting of scrubber ducts, contaminated building, lift stations including wet wells of sewage treatment plants, and manufacturing facilities for eliminating odoriferous gases from contaminated air, and particulate contaminants, grease, bacteria and viruses entrained in the gases.

30. A process as claimed in claim 17, wherein said mixture of nitrogen and oxygen ranges by volume from about 93% oxygen and 7% nitrogen to about 95% oxygen and 5% nitrogen.

31. A process as claimed in claim 17, wherein said mixture of nitrogen and oxygen is about 90% oxygen and 10% nitrogen.

32. An apparatus for the sanitizing of enclosed spaces in contaminated buildings and ductwork contained in said buildings for air conditioning, ventilating and heating systems and the like through a treatment of contaminated air, or surfaces in said enclosed spaces for the removal of odoriferous sulfur-containing gases, and/or microorganisms, and or non-gas phase grease therefrom utilizing wet particles of ozonated water reacting with the gases and/or grease, said apparatus comprising:

at least one atomizing nozzle arranged in said enclosed space, said at least one atomizing nozzle being supplied with flows of water, propellant gas, comprised of contaminated or uncontaminated air, and ozone produced from a mixture of nitrogen and oxygen, the water, propellant gas and ozone being admixed to form a spray of ozonated water droplets into said enclosed spaces; and a slotted vent tube housing the at least one atomizing nozzle, said slotted vent tube extending to the exterior of said enclosed space, said slotted vent tube receiving a flow of said contaminated air containing ozonated water droplets through said slots, wherein large-sized droplets coalesce within said slots and drain down along the surfaces of said vent tube and are recycled, whereby said droplets of ozonated water in said enclosed spaces eliminate odors from said odoriferous sulfur-containing gases, microorganisms and noxious particulates contained in said odoriferous sulfur-containing gases through a continuous in feed in low doses enabling nitrogen/oxygen mixtures in said droplets to render available low dosages of ozone for extended contact times.

33. An apparatus as claimed in claim 32, wherein a said atomizing nozzle is directed into said ductwork for duct disinfection wherein measurable ozone exists in the condensate of said droplets exiting from said ductwork.

34. An apparatus as claimed in claim 32, wherein said enclosed space defines a chamber of an industrial site containing oxidizable gas emitting from waste liquids; a polishing vent of a scrubber being operatively connected to said apparatus, said polishing vent including a coiled duct comprising said ductwork imparting turbulence to an air inlet flow so as to enable the reaction of ozonated water droplets for the elimination of said oxidizable gases and contaminants in said closed chamber.

35. An apparatus as claimed in claim 32, wherein said oxidizable gas causes said grease to become soluble in water so as to be for elimination from said enclosed spaces.

36. A process for the sanitizing of enclosed spaces in contaminated buildings and ductwork contained in said buildings for air conditioning, ventilating and heating systems and the like through a treatment of contaminated air or surface, in an enclosed space for the removal of odoriferous sulfur-containing gases therefrom utilizing wet particles of ozonated water reacting with the gases, said process comprising:

arranging at least one atomizing nozzle in said enclosed space;

supplying said at least one atomizing nozzle with flows of water, a propellant gas, comprised of contaminated or uncontaminated air, and ozone produced from a mixture of nitrogen and oxygen;

forming a spray of ozonated water droplets into said enclosed space by admixing the water, propellant gas and ozone in the at least one atomizing nozzle;

selectively condensing water droplets larger than 7 microns, present in said spray of ozonated water droplets, whereby said condensed water droplets are removed from said spray of ozonated water droplets; and recirculating water droplets equal to or smaller than 7 microns into said spray of ozonated water droplets.

37. A process as claimed in claim 36, wherein said atomizing nozzle is directed into said ductwork for duct disinfection wherein measurable ozone exists in the condensate of said droplets exiting from said ductwork.

38. A process as claimed in claim 36, wherein said odoriferous sulfur-containing gases cause said grease to become soluble so as to be eliminated from said enclosed space.

39. A process as claimed in claim 36, wherein said enclosed space defines a chamber of an industrial site containing oxidizable gas emitting waste liquids; a polishing vent of a scrubber being operatively connected to said enclosed space, said polishing vent including a coiled duct comprising said ductwork imparting turbulence to an air inlet flow so as to enable the maintenance of ozonated water droplets for the elimination of said oxidizable gases in said closed chamber.

* * * * *